United States Patent
D'Amelio, Sr. et al.

(10) Patent No.: US 7,214,392 B2
(45) Date of Patent: May 8, 2007

(54) PROCESS AND COMPOSITION FOR INHIBITING GROWTH OF MICROORGANISMS

(75) Inventors: Frank S. D'Amelio, Sr., Huntington, NY (US); Youssef W. Mirhom, Huntington Station, NY (US)

(73) Assignee: Bio-Botanica, Inc., Hauppauge, NY (US)

( * ) Notice: Subject to any disclaimer, the term of this patent is extended or adjusted under 35 U.S.C. 154(b) by 291 days.

(21) Appl. No.: 10/784,901

(22) Filed: Feb. 24, 2004

(65) Prior Publication Data

US 2004/0213861 A1    Oct. 28, 2004

Related U.S. Application Data

(60) Provisional application No. 60/449,437, filed on Feb. 25, 2003.

(51) Int. Cl.
    *A61K 36/53*    (2006.01)
    *A61K 36/54*    (2006.01)
    *A61K 36/71*    (2006.01)
    *A61K 36/00*    (2006.01)

(52) U.S. Cl. ............... 424/745; 424/739; 424/726; 424/725

(58) Field of Classification Search ............... None
    See application file for complete search history.

(56) References Cited

U.S. PATENT DOCUMENTS

| | | | |
|---|---|---|---|
| 4,380,506 A * | 4/1983 | Kimura et al. ............... 252/398 |
| 4,518,593 A | 5/1985 | Juvin et al. |
| 5,906,825 A * | 5/1999 | Seabrook et al. ............ 424/404 |
| 5,939,050 A | 8/1999 | Iyer et al. |
| 6,027,716 A | 2/2000 | Levin et al. |
| 6,106,838 A | 8/2000 | Nitsas |
| 6,106,851 A * | 8/2000 | Beerse et al. ................ 424/401 |
| 6,197,305 B1 | 3/2001 | Friedman et al. |
| 6,248,343 B1 * | 6/2001 | Jampani et al. .............. 424/405 |
| 6,296,880 B1 * | 10/2001 | Murad ......................... 424/616 |
| 6,306,450 B1 | 10/2001 | Bank et al. |
| 6,338,855 B1 * | 1/2002 | Albacarys et al. ........... 424/409 |
| 6,544,530 B1 | 4/2003 | Friedman |
| 6,551,628 B1 * | 4/2003 | Watson et al. ............... 424/725 |
| 2001/0005510 A1 * | 6/2001 | Garofano ..................... 424/405 |
| 2002/0034489 A1 * | 3/2002 | Wiegland et al. ......... 424/70.24 |
| 2003/0082130 A1 * | 5/2003 | Verdun et al. ............ 424/70.13 |
| 2003/0083212 A1 * | 5/2003 | Willard et al. ............... 510/137 |
| 2003/0124083 A1 * | 7/2003 | Filipski et al. ................ 424/73 |
| 2003/0176364 A1 * | 9/2003 | Ninkov ......................... 514/23 |

FOREIGN PATENT DOCUMENTS

| | | | |
|---|---|---|---|
| JP | 07267873 | * | 10/1995 |
| JP | 8-20510 | | 1/1996 |
| JP | 08020510 | * | 1/1996 |
| KR | 2002057448 | * | 7/2002 |

OTHER PUBLICATIONS

Castleman, M. The Healing Herbs. 1991. Rodale Press, Emmaus, PA., pp. 115-117, 201-204, 311-313, and 351-354.*
Ayoub, S. Planta Med. 1990. vol. 56, No. 6, pp. 644-645. DRUGU Abstract enclosed.*
Janssen et al. Pharm. Weekbl. Sci. Ed. 1988. vol. 10, No. 6, pp. 277-280, DRUGU Abstract enclosed.*
Janssen et al. Parm. Weekbl. Sci. Ed. 1986. vol. 8, No. 6, pp. 289-292, DRUGU Abstract enclosed.*

* cited by examiner

*Primary Examiner*—Christopher R. Tate
(74) *Attorney, Agent, or Firm*—Roylance, Abrams, Berdo & Goodman, L.L.P.

(57) ABSTRACT

A natural preservative composition obtained from plant materials provides antimicrobial activity for various compositions such as a food composition. The antimicrobial agent is effective in inhibiting the growth of gram-positive *Staphylococcus aureus*, gram-negative *Escherichia coli*, *Salmonella typhimurium*, *Klebsiella pneumoniae*, and *Pseudomonas aeruginosa*, acid-fast bacterium *Mycobacterium smegmatis*, the yeast *Candida albicans*. The antimicrobial agent has a MIC of 3.0 μl/ml capable of inhibiting these organisms. The antimicrobial agent includes mixtures of *Origanum vulgare* L., *Thymus vulgaris* L., *Cinnamomum zeylanicum* Nees, *Rosmarinum officinalis* L., *Lavandula officinalis* L., *Hydrastis canadensis* L. and olive leaf extract. The antimicrobial agent is an effective natural alternative to commonly used synthetic ingredients for product preservation.

42 Claims, No Drawings

PROCESS AND COMPOSITION FOR INHIBITING GROWTH OF MICROORGANISMS

CROSS-REFERENCE TO RELATED APPLICATION

This application claims the benefit under 35 U.S.C. § 119(e) of prior provisional application No. 60/449,437, filed Feb. 25, 2003, which is hereby incorporated by reference in its entirety.

FIELD OF THE INVENTION

The present invention is directed to a process for inhibiting the growth of microorganisms and to an antimicrobial composition. The invention is further directed to a composition containing a mixture of plant materials that is effective in inhibiting the growth of microorganisms and to a method of inhibiting the growth of microorganisms using the mixture of plant materials.

BACKGROUND OF THE INVENTION

Preservatives and antimicrobial agents have been used over the years to control or inhibit the growth of various microorganisms in various products and particularly food compositions. The increased use of antibiotics and antimicrobial agents and compositions has resulted in numerous pathogenic microorganisms developing new strains that are resistant to many of the commonly used antimicrobial and antibacterial agents.

Many of the commonly used food preservatives and microbial agents are synthetic compounds. In recent years, there has been an increased interest in avoiding or eliminating the use of synthetic compounds and in developing and promoting the use of natural materials. Plant materials are generally considered less toxic by the consumer and a more suitable natural alternative to synthetic compounds.

Various herbal and plant preparations are known for various uses. For example, one known composition is a mixture of *Echinaceae angustifoliae radix* and Plantago. This composition has been produced as an oral hygiene composition. Various reports have been produced showing antibacterial activity in the oral cavity and promoting general health of oral tissue.

Although various plant compositions have been produced, many of these have not been shown to be effective in inhibiting the growth of microorganisms. In addition, many of the commercially available compositions have not shown long antimicrobial activity. Fungal infections are common in humans, as well as other animals. The uncontrolled growth of many fungi can cause various diseases and discomfort to the animal. Topical antifungal preparations are commonly used, although many topically applied compositions may not be effective for certain strains.

One example of a composition containing botanical materials is disclosed in U.S. Pat. No. 6,197,305 to Friedman et al. The disclosed composition is stated to have antifungal properties, prolonged antifungal activity and good antibacterial activity. The antifungal composition contains an essential oil and an herbal extract.

U.S. Pat. No. 6,027,716 to Levin et al. discloses a composition containing an herbal extract and an essential oil. The components forming the resulting composition are disclosed as having a synergistic effect and antimicrobial activity. The composition includes cinnamon oil as the essential oil. The herbal extract is a mixture of Plantago, Hypericum, Echinacea and Propolis.

U.S. Pat. No. 5,939,050 to Iyer et al. discloses an antimicrobial composition containing two different antimicrobial agents for use in oral hygiene products. The compositions are disclosed as being effective to inhibit the growth of *Actinomyces viscosus, Fusobacterium nucleatum, Porphyromonas gingivalis, Streptococcus mutans*, and *Streptococcus sanguis*. The antimicrobial agents are plant oils and extracts and are combined to form a synergistic composition.

These compositions and preparations that have been previously available have exhibited some success. There is, however, a continuing need in the industry for an improved antimicrobial, antifungal and antibacterial composition.

SUMMARY OF THE INVENTION

The present invention is directed to a process for inhibiting the growth of various microorganisms and stabilizing compositions. The invention is also directed to an antimicrobial agent and an antimicrobial composition obtained from plant and botanical materials and extracts.

Accordingly, a primary aspect of the invention is to produce an antimicrobial agent and composition having antifungal and antibacterial properties. The composition contains an effective amount of a mixture of plant materials or plant extracts that together effectively inhibit the growth of microorganisms. The composition is used as a stabilizing agent for various compositions such as cosmetics and food products.

Another aspect of the invention is to provide an antimicrobial composition obtained from plant materials, plant extracts or essential oils obtained from the plant materials. In one preferred embodiment of the invention, the plant materials, plant extracts or essential oils are obtained from *Origanum vulgare* L., *Thymus vulgaris* L., *Cinnamomum zeylanicum* Nees, *Rosmarinus officinalis* L., *Lavandula officinalis* L., and *Hydrastis canadensis* L. The antimicrobial composition typically contains a mixture of the plant materials, plant extracts or oils in amounts effective to inhibit the growth of microorganisms.

The antimicrobial agent of the invention is particularly suitable for inhibiting the growth of microorganisms in various products and compositions that normally support the growth of microorganisms. The antimicrobial agent can be admixed with various compositions such as cosmetics and food products or applied to the surface of the food or other product to prolong the storage and shelf life of the food products. The antimicrobial agent can also be applied to the surface of an object to inhibit contamination.

Another aspect of the invention is to provide a method of inhibiting the growth of microorganisms by topically applying the antimicrobial agent of the invention to the skin of a patient. The antimicrobial agent can be dispersed in a suitable carrier or vehicle for topically applying to the skin of the patient.

Still another aspect of the invention is to provide an oral hygiene product containing an antimicrobial agent obtained from the botanical materials, extracts or essential oils. The oral hygiene composition can be in the form of a rinse or dentifrice that can be applied directly to the gums and mucosa surfaces.

A further aspect of the invention is to provide a method for inhibiting the growth of gram-positive bacteria, gram-negative bacteria, acid-fast bacteria and yeasts by contacting the microorganisms or a surface containing the microorganisms with an effective amount of an antimicrobial agent obtained from botanic materials, extracts or essential oils.

The aspects of the invention are basically attained by providing a process for inhibiting the growth of microorganisms. The process comprises the step of contacting the microorganisms or a surface containing the microorganisms with an effective amount of an antimicrobial composition. In one embodiment, the antimicrobial composition includes a mixture of plant materials comprising *Origanum vulgare* L., *Thymus vulgaris* L., *Rosmarinus officinalis* L., *Lavandula officinalis* L., and *Hydrastis canadensis* L. In another embodiment of the invention, the composition also contains *Cinnamomum zeylanicum* Nees in an amount effective to provide an antimicrobial and stabilizing effect.

The aspects of the invention are further attained by providing a shelf stable composition comprising a substrate, and an effective amount of an antimicrobial agent to inhibit the growth of microorganisms on or in the substrate. The antimicrobial agent includes a mixture of plant extracts comprising *Origanum vulgare* L., *Thymus vulgaris* L., *Rosmarinus officinalis* L., *Lavandula officinalis* L., and *Hydrastis canadensis* L. In another embodiment, the antimicrobial agent also contains *Cinnamomum zeylanicum* Nees in an amount effective to stabilize the composition and inhibit the growth of microorganisms.

The aspects of the invention are also attained by providing a preservative and stabilizing composition which comprises an antimicrobial agent. The antimicrobial agent is comprised of a mixture of plant materials and extracts selected from the group consisting of *Origanum vulgare* L., *Thymus vulgaris* L., *Rosmarinus officinalis* L., and *Lavandula officinalis* L. A carrier for the antimicrobial agent is provided. The antimicrobial agent is present in an amount effective to inhibit the growth of microorganisms. In one embodiment, the antimicrobial agent also includes a component selected from the group consisting of *Cinnamomum zeylanicum* Nees, *Hydrastis canadensis* L, olive leaf extract and mixtures thereof.

These and other aspects of the invention will become apparent from the following detailed description of the invention which disclose various embodiments of the invention.

DETAILED DESCRIPTION OF THE INVENTION

The present invention is directed to a process and composition for inhibiting the growth of various microorganisms. The invention is particularly directed to antimicrobial, antifungal and antibacterial compositions and preparations containing active components obtained from selected plant materials.

Many microorganisms are known to have an adverse effect on the health of animals, and particularly humans, as well as on the shelf life of foods and other products. The composition of the invention is effective in inhibiting the growth of microorganisms in various compositions and on various substrates in a manner to extend the shelf life of foods and to inhibit the spread of the microorganisms.

The composition of the invention includes an antimicrobial agent in an amount that is effective in providing the desired antimicrobial inhibiting effect. The antimicrobial agent is effective in inhibiting the growth of various microorganisms including, for example, *Staphylococcus aureus, Escherichia coli, Salmonella typhimurium, Klebsiella pneumoniae, Pseudomonas aeruginosa, Mycobacterium smegmatis, Candida albicans*, and *Aspergillus niger*. The antimicrobial agent is effective in inhibiting the growth of a broad range of gram-positive and gram-negative bacteria, acid-fast bacteria, molds, yeasts and fungi.

The antimicrobial agent of the invention is a mixture of botanical or plant materials and extracts containing active compounds that are combined in a manner to provide antimicrobial activity. The antimicrobial agent and compositions containing the antimicrobial agent can contain the whole plant, extracts of the plant and mixtures thereof. In preferred embodiments, the botanical components are extracts, oils or fractions containing the active components. The antimicrobial agent in one preferred embodiment of the invention is a mixture of botanical extracts and oils of *Origanum vulgare* L., *Thymus vulgaris* L., *Cinnamomum zeylanicum* Nees, *Rosmarinus officinalis* L., *Lavandula officinalis* L., and *Hydrastis canadensis* L. With the exception of *Hydrastis canadensis* L., each of the botanical materials are present in an amount of about 5 wt % to about 40 wt % based on the total weight of the antimicrobial agent. Due primarily to its limited solubility, *Hydrastis canadensis* L. is included in amounts of 0.1 wt % or less, and typically 0.01 wt % or less. The botanical materials are preferably combined in synergistic amounts to attain antimicrobial activity for one or more target microorganisms to be inhibited.

In preferred embodiments of the invention, extracts of the botanical materials are mixed together in proportions to provide the desired antimicrobial activity. The ratio of the components can also be adjusted to increase the antimicrobial activity or selectivity for a target microorganism. In various embodiments of the invention, the antibacterial composition contains about 20 to 40 wt % *Origanum vulgare* L., about 20 to 40 wt % *Thymus vulgaris* L., about 10 to 20 wt % *Cinnamomum zeylanicum* Nees, about 10 to 30 wt % *Rosmarinus officinalis* L. and about 5 to 15 wt % *Lavandula officinalis* L. In one preferred embodiment, the antimicrobial composition also contains about 0.00 1 to about 0.01 wt % and typically about 0.001 wt % to 0.003 wt % of *Hydrastis canadensis* L. A particularly suitable antimicrobial composition comprises about 30 wt % *Origanum vulgare* L., about 30 wt % *Thymus vulgaris* L., about 10 wt % *Cinnamomum zeylanicum* Nees, about 20 wt % *Rosmarinus officinalis* L., about 0.002 wt % *Hydrastis canadensis* L., and the balance (about 10 wt %) *Lavandula officinalis* L.

In one preferred embodiment, the antimicrobial agent includes about 20 wt % to about 40 wt % *Origanum vulgare* L., about 20 wt % to about 40 wt % *Thymus vulgaris* L., about 10 wt % to about 30 wt % *Rosmarinus officinalis* L., and about 5 wt % to about 15 wt % *Lavandula officinalis* L. The antimicrobial agent can also contain about 0.001 wt % to about 0.01 wt % *Hydrastis canadensis* L., about 0.001 wt % to about 0.005 wt % olive leaf extract, and mixtures thereof. In further embodiments, the antimicrobial agent can include an effective amount of the cinnamon bark extract to inhibit the growth of *S. typhimurium* and *P. aeruginosa*.

The botanical materials can be used in the form of the leaves, flowers, stems of the plant and mixtures thereof that have been dried and reduced to fine particles or powders. The plant materials can be reduced by grinding, pulverizing or macerating. The dried plant materials can be mixed in a suitable mixing or blending apparatus and used as a dry or substantially dry powder. In other embodiments, the powder can be dispersed in a suitable carrier or vehicle that can be applied to the environment or surface where the antimicrobial effect is desired.

In one preferred embodiment, the botanical materials are in the form of an extract or essential oil obtained from the plant materials. One or more of the botanical materials can be provided in the form of an extract or essential oil that is combined with a dry powder of the remaining plant materials. The extracts and essential oils are generally a mixture of esters, aldehydes, alcohols, ketones and terpenes obtained from the botanical materials. The essential oils can be prepared by a number of known processes that are able to recover the essential oils and active compounds from the plant materials.

One suitable process for preparing the extracts is by subjecting the plant materials to a distillation process. In this process, the plant material is macerated and heated in an amount of water for sufficient time to remove the water-extractable components. The resulting mixture is then distilled with steam to remove the organic components with the steam. The steam and organic components are then condensed and collected in a suitable collection vessel. The resulting oil phase is then separated from the aqueous phase by standard separation processes. The essential oil component is then purified as needed.

Alternatively, the botanical materials can be obtained and used as a tincture. The tincture can be obtained by extracting the active compounds using a solvent or extracting medium. The solvent can be an aqueous, organic solvent or mixture thereof. Examples of organic suitable solvents include glycerin, propylene glycol, and ethanol. In other embodiments, the extracting solvent is an aqueous/ethanol mixture that can contain about 10% to about 90% ethanol by volume. The botanical materials are generally macerated in the presence of the selected solvent. The solvent is allowed to remain in contact with the botanical materials for a suitable length of time to extract the active compounds before filtering to remove the solid materials. The filtrate is collected as the extract or tincture. The extract can be further purified and the concentration adjusted by evaporating the solvent or adding additional solvent. In one embodiment, the solvent in the tincture or extract is evaporated to obtain a residue or extract. The resulting extract can be in the form of a dry powder, oil or paste depending on the recovered fraction or compounds extracted from the botanical materials.

The extracts can also be obtained by placing the botanical materials in a column and percolating with the solvent by passing the solvent through the column. Percolation is desirable in some instances where the volume of solvent used can be minimized. The volume of solvent can be controlled by adjusting the flow rate through the column. Changing the flow rate and volume of the solvent can determine the make-up of the final extract for some plant materials that contain constituents with varying solubilities.

The extraction process can be carried out in an extraction vessel with a mixture of the plant material in hot water heated to about 90° C. for several hours, typically about 5–8 hours. The liquid material is then collected and then passed through a suitable separation column to purify the active components of the extract. Examples of separation media for use in the column include polystyrene, polyacrylic acid esters and polymethacrylic acid esters.

The botanical materials, extracts and/or essential oils are blended in a suitable ratio to provide the desired antimicrobial and stabilizing activity for the intended use. The botanical materials contain various compounds that can have an effect on the antimicrobial properties. The antimicrobial properties can be modified by altering the ratio of the components to be more or less selective for a specific microorganism.

The plant materials, oils and extracts have been found to have a synergistic effect when combined to provide effective antimicrobial activity that is not found in the plant materials individually. The plant materials have been found to contain various compounds that when combined in the mixture of botanical materials exhibit antimicrobial properties. For example, *Origanum vulgare* L., and *Thymus vulgaris* L. contain carvacrol and thymol. *Cinnamomuin zeylanicum* Nees contains primarily cinnamaldehyde and eugenol. *Rosmarinus officinalis* L. contains 1,8-cineole, camphor, α-pinene and small amounts of rosmarinic acid. *Lavandula officinalis* L. contain linalyl acetate and linalol. *Hydrastis canadensis* L contain berberine and hydrastine alkaloids. In one embodiment of the invention, the antimicrobial agent is a mixture of the botanical materials, extracts or essential oils to provide antimicrobial amounts of carvacrol, thymol, cinnamaldehyde, eugenol, cineole, camphor, α-pinene, rosmarinic acid, linalol, linalyl acetate, berberine and hydrastine where the components are provided in an amount to obtain an antimicrobial effect.

The *Cinnamomum zeylanicum* Nees or cinnamon bark fraction is particularly effective in inhibiting the growth of *S. typhimurium* and *P. aeruginosa* which are normally resistant to a number of common antibacterial agents. The antibacterial agent of the invention containing cinnamon bark extract was found to be effective in inhibiting the growth of *S. typhimurium* with a MIC of 0.075% and *P. aeruginosa* with a MIC of 0.15% by volume of the agar medium.

In some compositions and processes for using the compositions, it is desirable to avoid the use of cinnamaldehyde so that the cinnamon bark extract (*Cinnamomum zeylanicum* Nees) is not used in the antimicrobial agent. The antimicrobial agent without the cinnamon bark extract has been found to inhibit the growth of *S. typhimurium* at a MIC of 0.35% and *P. aeruginosa* with a MIC of 0.55% by volume based on the volume of the agar medium. In embodiments where the cinnamon bark extract is not used, olive leaf extract (*Olea europaea*) can be added in an amount to enhance the antimicrobial properties of the composition. Olive leaf extract contains Oleuropein which has been found to be a potent antimicrobial agent for some microorganisms. The olive leaf extract is only slightly soluble in the oils of the remaining extracts and is used in amounts of 1 wt % or less. Typically, the olive leaf extract is used in amounts of about 0.01 wt % or less.

In one embodiment, the antimicrobial composition comprises about 33.3 wt % *Origanum vulgare* L., about 33.3 wt % *Thymus vulgaris* L., about 22.3 wt % *Rosmarinus officinalis* L., about 0.002 wt % *Hydrastis canadensis* L., and the balance (about 10 wt %) *Lavandula officinalis* L. In a further embodiment, the composition also contains about 0.001 wt % olive leaf extract.

The antimicrobial agent containing the components of the botanical materials can be used directly as obtained or can be combined with a suitable carrier or vehicle in the form of an antimicrobial composition. The carrier is typically a liquid, solid, gel or paste. In various embodiments, the composition contains about 0.1 wt % to about 20 wt % of the antimicrobial agent. In embodiments where the antimicrobial agent is used as food preservative, the antimicrobial agent is added or combined with the food product in an amount of less than 1 wt %. The composition containing the antimicrobial agent can be in the form of a topical liquid, lotion, cream or gel for applying topically to the skin of a patent in need of treatment with the antimicrobial agent.

Examples of suitable carriers for the antimicrobial agent include water glycerol, ethanol, mineral oil and the like. The composition can also contain suitable humectants such as sorbitols and polyethylene glycols depending on the intended use.

In other embodiments, the antimicrobial composition can contain binders or thickening agents such as silica precipitates, carboxymethylcellulose, carboxyvinyl polymers, xanthan gum and carrageenan gum. Suitable surfactants include sodium lauryl sulfate and dodecylbenzene sulfonate. Flavorants, fragrances and anti-caking agents, as known in the art, can also be included.

In one embodiment of the invention, a food product is produced containing an effective amount of the antimicrobial agent or antimicrobial composition. The antimicrobial agent is generally dispersed in the food product to inhibit the growth of microorganisms, mold and fungi. The antimicrobial agent can be used with a dispersing agent or emulsifier as needed to keep the antimicrobial agent dispersed or suspended in the food product. The antimicrobial agent can be suspended in or mixed with a suitable food compatible carrier. In other embodiments, the antimicrobial agent can be applied as a coating on the surface of the food product.

Oral compositions, such as dentifrices and oral rinses, can be prepared containing an amount of the antimicrobial agent to inhibit the growth of bacteria in the mouth. The dentifrice and oral rinse can include typical components such as dispersing agents, humectants and thickening agents to maintain the antimicrobial agent in suspension as well as flavoring agents, acidulants and coloring agents.

In one embodiment of the invention, the antimicrobial composition contains an effective amount of the antimicrobial agent for topically applying to the skin of a patient. The composition can be in the form of a liquid, lotion, cream or gel that can be applied directly to the skin and to scratches, abrasions and minor cuts. The antimicrobial agent can also be added to a cleanser such as a detergent, soap or cleaning agent. The cleaner can be hand or body soap, a hard surface cleaner or laundry detergent.

The process of the invention inhibits the growth of microorganisms by contacting the microorganisms with an effective amount of the antimicrobial agent or by applying the antimicrobial agent to a base material or substrate where the microorganisms come in contact. The base material can be a food product or a solid surface. In one embodiment, the base material is capable of supporting the growth of microorganisms. The effective amount of the antimicrobial agent can vary depending on the particular microorganism to be inhibited and expected concentration of the microorganisms to be encountered. The antimicrobial agent is typically used to provide a minimum inhibitory concentration (MIC) amount. In one preferred embodiment, the antimicrobial agent is obtained from a mixture of plant materials including *Origanum vulgare* L., *Thymus vulgaris* L., *Cinnamomum zeylanicum* Nees, *Rosmarinus officinalis* L., *Lavandula officinalis* L., and *Hydrastis canadensis* L. In one embodiment, the plant materials are used in substantially equal amounts. The antimicrobial agent containing the mixture of the plant materials have an MIC about 1.5 µl/ml or less for gram-negative and gram-positive bacteria. The antimicrobial agent has an MIC of 1.5 µl/ml or less for *E. coli*, an MIC of 0.75 µl/ml or less for *Klebsiella pneumoniae*, and an MIC of 0.5 µl/ml for *Mycobacterium*.

The growth of the microorganisms on a substrate is inhibited by contacting a substrate with the antimicrobial agent. The substrate can be a food product or other material that typically supports the growth of microorganisms. In other embodiments, the antimicrobial agent is dispersed within the substrate.

The antimicrobial agent includes a mixture of the botanical materials in amounts and proportions to provide the desired antimicrobial properties and effectiveness in inhibiting the growth of the target microorganisms. The antimicrobial agent of the invention includes the plant materials, extracts or essential oils to provide antimicrobial inhibiting amounts of a compound selected from the group consisting of carvacrol, thymol, cinnamaldehyde, eugenol, cineole, camphor, α-pinene, rosmarinic acid, linalol, linalyl acetate, berberine and hydrastine, and mixtures thereof. Preferably, the antimicrobial agent contains a mixture of the compounds or a mixture of the botanical materials in amounts to provide the antimicrobial effect.

The antimicrobial agent can also be used to produce a shelf-stable composition where the composition includes a base material or substrate. The substrate can be a solid, liquid or semi-solid.

The antimicrobial agent of the invention has been found to be effective in inhibiting the growth of various bacteria and fungi. The effectiveness of the antimicrobial agent in many situations has been found to be at least as effective and under some conditions, more effective than conventional commercially available antimicrobial agents and preservatives in inhibiting the growth of bacteria and fungi on a substrate. In the following examples, the antimicrobial agent is shown to have a lower Minimum Inhibitory Concentration (MIC) than standard preservatives and antibacterial agents for certain gram-positive and gram-negative organisms. The Minimum Inhibitory Concentration refers to the minimum concentration in micrograms per milliliter of an antimicrobial agent at which no bacteria or microorganism growth are observed. At concentrations at or above the Minimum Inhibitory Concentration, the antimicrobial agent is effective in killing or inhibiting the growth and reproduction of the microorganisms. At concentrations below the Minimum Inhibitory Concentration, the antimicrobial agent is not effective in inhibiting the growth of microorganisms.

It has been observed that the combination of botanical materials or extracts of *Origanum vulgare* L., *Thymus vulgaris* L., *Cinnamomum zeylanicum* Nees, *Rosmarinus officinalis* L., *Lavandula officinalis* L., and *Hydrastis canadensis* L. have a lower MIC than the conventional preservatives such as phenyloxyethanol, phenylethyl alcohol, and a mixture of methylparabens/propylparabens in a ratio of 5:4. The antimicrobial agent of the invention has been found to have a MIC of 3.0 µl/ml for gram-positive *Staphylococcus aureus*, gram-negative *Escherichia coli, Salmonella typhimurium, Klebsiella pneumoniae*, and *Pseudomonas aeruginosa*, acid-fast bacterium *Mycobacterium smegmatis*, and *M. tuberculosis*, the yeast *Candida albicans*, and the filamentous mold *Aspergillus niger*. The following non-limiting examples demonstrate the effectiveness of the antimicrobial agent and compositions containing the antimicrobial agent.

EXAMPLE 1

An antimicrobial agent was prepared from a mixture of botanical extracts containing 30 wt % *Origanum vulgare* L., 30 wt % *Thymus vulgaris* L., 10 wt % *Cinnamomum zeylanicum* Nees, 20 wt % *Rosmarinus officinalis* L., about 9.998 wt % *Lavandula officinalis* L., and 0.002 wt % *Hydrastis canadensis* L. The leaves from the plant materials were macerated and the various compounds and oils extracted. The resulting extracts were combined to form the antimicrobial agent.

EXAMPLE 2

The Agar Dilution susceptibility method was used to test the effectiveness of the antimicrobial composition of Example 1. The organisms used were *S. aureus* ATCC 29213, *E. coli* ATCC 25922, *S. typhimurium* ATCC 14028, *K. pneumoniae* ATCC 10031, *P. aeruginosa* ATCC 27853, *C. albicans* ATCC 10231, and *M. smegmatis* ATCC 14468. The organisms were maintained on Tryptic Soy Agar (TSA) slants. For each week, the organisms were cultured in 10 ml of Tryptic Soy Broth (TSB). After incubation at 37° C. for 17 hours (48 hours for *M. smegmatis*), the organism suspensions were diluted with 10 ml of sterile saline as shown in Table 1. The mold *Aspergillus niger* was sustained on a Sabouraud Dextrose Agar slant. The sample was then cultured in 10 ml of Tryptic Soy Broth and incubated for 7 days at 22° C. The mold was then diluted in 0.1% Tween 80 in saline. The diluted bacteria and yeast organisms were then inoculated onto the prepared sample plates with a 1 µl loop. The mold *Aspergillus niger* was added to prepared sample tubes with a 100 µl pipette.

TABLE 1

Microorganism Dilutions

| | |
|---|---|
| *S. aureus* ATCC 29213 | 100 µl susp/10 ml saline |
| *E. coli* ATCC 25922 | 100 µl susp/10 ml saline |
| *S. typhimurium* ATCC 14028 | 100 µl susp/10 ml saline |
| *K. pneumoniae* ATCC 10031 | 100 µl susp/10 ml saline |
| *M. smegmatis* ATCC 14468 | Undiluted |
| *C. albicans* ATCC 10231 | 1 ml susp/10 ml saline |
| *P. aeruginosa* ATCC 27853 | 1 µl susp/10 ml saline |
| *A. niger* ATCC 16404 | 1 µl susp/10 ml 0.1% Tween 80 in saline |

Phenyloxyethanol (PE), phenylethyl alcohol (PEA) and methyl/propylparabens (MP) in a ratio of 5:4 were initially screened at their commonly recommended effective concentrations of 0.3% v/v (3 µl/ml); 1% v/v (10 µl/ml); and 0.18% w/v (1 mg methyl and 0.8 mg propylparaben/ml), respectively. The antimicrobial agent was used at an initial concentration of 0.15% v/v (1.5 µl/ml).

The sample plates for the bacteria and yeast were prepared as follows:
Prepare 10 ml tubes of TSA and allow to cool to 50° C.,
Add the calculated amount of the preservative or antimicrobial agent to 100 µl dimethylsulfoxide (DMSO) to achieve the specified concentration per ml TSA when 100 µl of the DMSO solution are added to a test tube containing 10 ml of TSA,
Vortex to homogenize the mixture in TSA,
Pour TSA and the preservative or antimicrobial agent into a properly labeled Petri dish,
Allow to cool overnight at room temperature.

The sample for the mold *Aspergillus niger* was prepared as follows:
Prepare 10 ml tubes of Tryptic Soy Broth (TSB),
Add the calculated amount of the sample to 100 µl dimethylsulfoxide (DMSO) to achieve the specified concentration per ml TSB. Then 100 µl of the DMSO is added to a test tube containing 10 ml of TSB,
Vortex to homogenize the mixture in TSB,
Add 100 µl of *Aspergillus niger* suspension to a tube of TSB not inoculated with any sample as a positive control.

The prepared sample plates were divided into seven sections and the plates labeled according to the preservative or antimicrobial agent. Each section was labeled according to the microorganism to be applied to each section. The diluted organism suspensions were inoculated onto their appropriate section with a 1 µl loop, streaking radially from the center to the outer edge of the plate. A negative control plate was prepared without a preservative or antimicrobial agent of Example 1. The plates were then incubated at 37° C. for 48 hours, recording the results at 24 and 48 hours.

The prepared sample tubes were inoculated with 100 µl of the mold *Aspergillus niger* suspension to produce a final mold spore concentration in each sample tube of $1 \times 10^4$ to $1 \times 10^5$ spores/ml. The prepared sample tubes of TSB were incubated at 37° C. for 5 days with the results being recorded at 3 and 5 days.

The results for the bacteria and yeast were scored in relation to the growth present on the negative control plate without an antimicrobial agent. Growth (G) was noted when there was full growth visible and the organism was not affected. Partial activity (P) was recorded when the organism was morphologically altered or growth was partially inhibited, and no growth (I) was recorded when there was total inhibition. The results are recorded in Table 2.

The results for *Aspergillus niger* were scored in relation to the growth present in the positive control tube. The growth (G) was noted when there was full growth visible as determined by the tube appearing cloudy to the same extent as the positive control tube. Partial activity (P) was recorded when the sample tube of TSB was less turbid than the control tube. No growth (I) was recorded when there was total inhibition and broth in the tube appeared clear.

When a result of (I) was scored, the MIC was established by performing the dilutions as indicated in Table 2 and Table 3. In this example and the tables, the amount of the antimicrobial agent is expressed in terms of the volume of antimicrobial sample. The concentration of the antimicrobial agent of 1 µl/ml corresponds to 1 µg (microgram)/ml of the antimicrobial agent. The MIC obtained was confirmed by three consecutive results. DMSO was used to solubilize the test samples and help to diffuse the lipophilic ingredients into the agar. DMSO was used at a concentration not exceeding 1%.

TABLE 2

Antimicrobial Screening Results

| SAMPLE/ml of Agar | MICROORGANISMS* | | | | | | | |
|---|---|---|---|---|---|---|---|---|
| | 1 | 2 | 3 | 4 | 5 | 6 | 7 | 8 |
| Antimicrobial Agent of Example 1 | | | | | | | | |
| 0.25 µl/ml | G | G | G | G | P | P | G | G |
| 0.5 µl/ml | G | G | G | P | I | I | G | P |
| 0.75 µl/ml | P | G | G | I | I | I | G | I |
| 1.0 µl/ml | P | G | G | I | I | I | P | I |
| 1.5 µl/ml | I | I | P | I | I | I | P | I |
| 2.0 µl/ml | I | I | P | I | I | I | I | I |
| 3.0 µl/ml | I | I | I | I | I | I | I | I |
| Phenoxyethanol (PE) | | | | | | | | |
| 1.0 µl/ml | G | G | G | G | P | P | P | P |
| 2.5 µl/ml | G | P | P | P | I | I | P | I |
| 3.0 µl/ml | G | P | P | I | I | I | I | I |
| 5.0 µl/ml | G | I | I | I | I | I | I | I |
| 10.0 µl/ml | I | I | I | I | I | I | I | I |
| Phenylethyl Alcohol (PEA) | | | | | | | | |
| 0.75 µl/ml | G | G | G | G | G | P | P | G |
| 1.5 µl/ml | G | P | P | I | P | P | P | P |
| 3.0 µl/ml | G | I | I | I | I | I | P | I |
| 5.0 µl/ml | P | I | I | I | I | I | I | I |
| 6.0 µl/ml | I | I | I | I | I | I | I | I |

TABLE 2-continued

Antimicrobial Screening Results

| SAMPLE/ml of Agar | MICROORGANISMS* | | | | | | | |
|---|---|---|---|---|---|---|---|---|
| | 1 | 2 | 3 | 4 | 5 | 6 | 7 | 8 |
| Methylparaben and Propylparaben (MP) | | | | | | | | |
| 0.9 mg/ml | G | G | G | G | G | G | G | G |
| 1.8 mg/ml | G | G | G | G | G | G | G | P |
| 3.6 mg/ml | G | G | G | G | G | G | G | I |
| 5.4 mg/ml | P | G | G | G | I | I | P | I |
| 7.2 mg/ml | P | P | P | P | I | I | P | I |
| 10.8 mg/ml | I | P | P | I | I | I | P | I |
| 16.2 mg/ml | I | I | P | I | I | I | P | I |
| 21.6 mg/ml | I | I | I | I | I | I | I | I |

Abbreviations:
G = growth,
P = partial inhibition,
I = inhibition (no growth)
Results are scored in relation to the growth present on the negative control plate.
*Microorganisms:
(1) *Staphylococcus aureus*
(2) *Escherichia coli*
(3) *Salmonella typhimurium*
(4) *Klebsiella pneumoniae*
(5) *Mycobacterium smegmatis*
(6) *Candida albicans*
(7) *Pseudomonas aeruginosa*
(8) *Aspergillus niger*

The Minimum Inhibitory Concentrations for the antimicrobial agent of Example 1 and the other preservatives tested on each individual microorganism are presented in Table 3. The antimicrobial agent of Example 1 has the lowest MIC (3.0 µl/ml) capable of inhibiting all the tested organisms (i.e., gram-positive, gram-negative, acid-fast bacteria and yeast). Only 2.0 µl/ml were required to inhibit all microorganisms tested except *S. typhimurium* and 1.5 µl/ml was found to inhibit all microorganisms except *P. aeruginosa* and *S. typhimurium*. Much higher concentrations of the other preservatives were required to inhibit all microorganisms tested. Complete inhibition of all of the microorganisms tested required 6.0 µl/ml of PEA, 10.0 µl/ml of PE and more than 7.2 mg/ml of MP.

The antimicrobial agent of the invention has been found to be effective in inhibiting the growth of *Staphylococcus aureus* (*S. aureus*) at a MIC of 1.5 µl/ml. Many other known preservatives such as phenoxyethanol require four times this amount to inhibit the growth of *S. aureus*. Phenylethyl alcohol is commonly used at 0.3 wt % and methylparaben and propylparaben mixtures are commonly used as 0.18 wt %. These conventional preservatives at these concentrations have been found to have no effect on *S. aureus*. *S. aureus* is frequently part of the normal human flora and is a common pathogen that causes skin infections, food poisoning, and toxic shock syndrome.

*E. coli*, *S. typhimurium* and *K. Pneumoniae* are gram-negative rods that cause gastroenteritis and a variety of infections in humans. The antimicrobial agent of the invention has been found to inhibit the growth of these microorganisms at low concentrations compared with conventional preservatives. For example, *K. Pneumoniae* is inhibited at a concentration of 0.75 µl/ml, *E. coli* is inhibited at a concentration of 1.5 µl/ml and *S. typhimurium* is inhibited at a concentration of 3.0 µl/ml.

*M. smegmatis* is an acid-fast bacterium similar to *M. tuberculosis*, which is a highly communicable intercellular parasitic bacterium that is always associated with infection. The antimicrobial agent of Example 1 is able to inhibit the acid-fast bacterium at a concentration of 0.5 µl/ml while other preservatives needed a concentration ranging from 5 to 10 times higher.

TABLE 3

Minimum Inhibitory Concentration (MIC)
(sample/ml of agar)

| | Antimicrobial Agent of Example 1 | Phenoxyethanol | Phenylethyl Alcohol | Methylparaben & Propylparaben |
|---|---|---|---|---|
| *S. aureus* ATCC 25213 | 1.0 µl/ml | 10.0 µl/ml | 6.0 µl/ml | 10.8 mg/ml |
| *E. coli* ATCC 25922 | 1.0 µl/ml | 5.0 µl/ml | 3.0 µl/ml | 16.2 mg/ml |
| *S. typhimurium* ATCC 14028 | 1.0 µl/ml | 5.0 µl/ml | 3.0 µl/ml | 21.6 mg/ml |
| *K. Pneumoniae* ATCC 10031 | 1.0 µl/ml | 5.0 µl/ml | 1.5 µl/ml | 10.8 mg/ml |
| *M. smegmatis* ATCC 14468 | 0.5 µl/ml | 2.5 µl/ml | 3.0 µl/ml | 5.4 mg/ml |
| *C. albicans* ATCC 10231 | 0.5 µl/ml | 2.5 µl/ml | 3.0 µl/ml | 5.4 mg/ml |
| *P. aeruginosa* ATCC 27853 | 2.0 µl/ml | 5.0 µl/ml | 5.0 µl/ml | 21.6 mg/ml |
| *A. niger* ATCC 16404 | 0.75 µl/ml | 2.5 µl/ml | 3.0 µl/ml | 3.6 mg/ml |

*C. albicans* is the species of yeast most often isolated from clinical specimens and can cause infection of the skin, nails and mucous membranes. It is also a source of diaper rash, certain vaginal and gastrointestinal infections. The antimicrobial agent of Example 1 was able to inhibit the yeast at a concentration lower than 0.5 µl/ml while PE, PEA and MP could inhibit it at concentrations ranging from 5 to 10 times higher.

EXAMPLE 3

The mold *Aspergillus niger* ATCC 16404 was selected for the antifungal testing and maintained on Sabouraud Dextrose Agar. *Aspergillus niger* is a mold that commonly causes opportunistic infections in humans. Spores are prevalent in soil and on decaying organic matter. *Aspergillus niger* is also a common cause of contamination in products. The organism was cultured in 10 ml of Tryptic Soy Broth for 7 days at 22° C. After incubation, 1 ml of mold culture was added to 10 ml of 0.1% Tween 80 solution in sterile saline to achieve a spore concentration of 0.5 McFarland ($1 \times 10^8$ spores/ml). This concentration was determined by visual comparison to a 0.5 McFarland standard. The macro-dilution broth susceptibility method was utilized to limit the amount of airborne mold spores by suspending them in liquid in a capped test tube as opposed to the agar dilution method used in previous research.

The antimicrobial agent of Example 1 and preservatives phenoxyethanol, phenylethyl alcohol and methyl and propyl parabens (5:4) were initially screened at a concentration of 0.1%. The samples were prepared as follows:

Prepare 10 ml tubes of Tryptic Soy Broth (TSB).

Add sample to 100 μl of DMSO (dimethylsulfoxide) to achieve specified concentration. (11 μl sample +100 μl DMS0 for 0.1% concentration).

Pipette 100 μl of preservatives in DMSO into one 10 ml tube TSB.

Vortex to homogenize mixture in TSB.

Add 100 μl of A. niger suspension to each of the tubes.

Add 100 μl of A. niger suspension to a tube of TSB without a preservative as a negative control sample.

The final concentration of mold spores in each sample was $1 \times 10^4$–$1 \times 10^5$ spores/ml. The prepared tubes of TSB were incubated at 37° C. for 5 days, and the results recorded at 3 and 5 days.

Each sample was tested for antifungal activity against *Aspergillus niger*. Concentrations were increased or decreased to determine the minimum inhibitory concentration (MIC) of each sample. When a MIC had been reached, the sample was tested multiple times at that concentration to confirm the result.

The results were scored in relation to the growth present in the negative control tube. Growth (G) was noted when there was full growth visible (i.e., the tube appeared as cloudy as the negative control tube). Partial activity (P) was recorded when the sample tube of TSB was less turbid than the control tube, and now growth (I) was recorded when there was total inhibition and the broth in the tube appeared clear. When a result of (I) was scored, the MIC was established by performing the appropriate dilutions. The results are recorded in the following Table 4.

TABLE 4

Antifungal Screening Results
*Aspergillus niger* ATCC 16404

| Antimicrobial Agent of Example 1 | 0.25 μl/ml G | 0.5 μl/ml P | 0.75 μl/ml I | 1.0 μl/ml I | 1.5 μl/ml I | 2.5 μl/ml I |
|---|---|---|---|---|---|---|
| Phenoxyethanol | 0.25 μl/ml G | 0.5 μl/ml G | 0.75 μl/ml G | 1.0 μl/ml P | 1.5 μl/ml P | 2.5 μl/ml I |
| Phenylethyl Alcohol | 0.25 μl/ml G | 0.5 μl/ml G | 0.75 μl/ml G | 1.0 μl/ml P | 1.5 μl/ml P | 2.5 μl/ml I |
| Methyl/Propylparaben | | | | 0.9 μl/ml G | 1.8 μl/ml P | 2.7 μl/ml I |

Abbreviations:
G = growth,
P = partial inhibition,
I = inhibition (no growth).
Results are scored in relation to the growth present in the negative control tube.

The result for the minimum inhibitory concentrations against fungi for the antimicrobial agent of Example 1 and the preservatives are presented in Table 5. The antimicrobial agent of Example 1 is shown to have the lowest MIC (0.75 μl/ml) capable of inhibiting the *Aspergillus niger*.

TABLE 5

Minimum Inhibitory Concentration (MIC)

| | Antimicrobial Agent of Example 1 | Phenoxyethanol | Phenylethyl Alcohol | Methylparaben & Propylparaben |
|---|---|---|---|---|
| *A. niger* ATCC 16404 | 0.75 μl/ml | 2.5 μl/ml | 2.5 μl/ml | 2.7 μl/ml |
| *C. albicans** ATCC 10231 | 0.5 μl/ml | 2.5 μl/ml | 3.0 μl/ml | 5.4 μl/ml |

The yeast *C. albicans* was tested in a previous trial and is presented herein to express the total antifungal properties of each sample

*Aspergillus niger* is a rapid growing hyaline mold whose spores are ubiquitous in nature. Therefore, it is a common fungal contaminant, and an opportunistic pathogen in humans. It may also cause black mold rot on a variety of fruits and vegetables.

EXAMPLE 4

An antimicrobial agent was prepared from a mixture containing 0.002 *Hydrastis canadensis* L., 0.001 wt % *Olea europaea*, 33.3 wt % *Origanum vulgare* L. extract, 33.3 wt % *Thymus vulgaris* L. extract, 22.2 wt % *Rosmarinus officinalis* L. extract, and the balance *Lavandula officinalis* L. extract (about 8.99 wt %).

The antimicrobial activity of this composition was determined using the Agar Dilution susceptibility test. The microorganism samples and agar samples were prepared in the same manner as in Example 2. The test results and MIC were determined according to the method of Example 2. The test results are shown in Tables 6 and 7.

TABLE 6

| SAMPLE/ml of Agar | MICROORGANISMS* | | | | | | | |
|---|---|---|---|---|---|---|---|---|
|  | 1 | 2 | 3 | 4 | 5 | 6 | 7 | 8 |
| 0.5 μl/ml | G | G | G | G | G | G | G | G |
| 0.75 μl/ml | G | G | G | G | P | G | G | P |
| 1.0 μl/ml | G | G | G | I | I | I | G | I |
| 1.5 μl/ml | P | G | G | I | I | I | G | I |
| 2.0 μl/ml | I | I | P | I | I | I | G | I |
| 3.0 μl/ml | I | I | P | I | I | I | P | I |
| 3.5 μl/ml | I | I | I | I | I | I | P | I |
| 4.0 μl/ml | I | I | I | I | I | I | P | I |
| 4.5 μl/ml | I | I | I | I | I | I | P | I |
| 5.0 μl/ml | I | I | I | I | I | I | P | I |
| 5.5 μl/ml | I | I | I | I | I | I | I | I |

Abbreviations:
G = growth,
P = partial inhibition,
I = inhibition (no growth)
Results are scored in relation to the growth present on the negative control plate.
*Microorganisms:
(1) *Staphylococcus aureus*
(2) *Escherichia coli*
(3) *Salmonella typhimurium*
(4) *Klebsiella pneumoniae*
(5) *Mycobacterium smegmatis*
(6) *Candida albicans*
(7) *Pseudomonas aeruginosa*
(8) *Aspergillus niger*

TABLE 7

Minimum Inhibitory Concentration (MIC)
(sample/ml of agar or broth)

| | Antimicrobial Agent of Example 4 |
|---|---|
| *S. aureus* ATCC 25213 | 2.0 μl/ml |
| *E. coli* ATCC 25922 | 2.0 μl/ml |
| *S. typhimurium* ATCC 14028 | 3.5 μl/ml |
| *K. Pneumoniae* ATCC 10031 | 1.0 μl/ml |
| *M. smegmatis* ATCC 14468 | 1.0 μl/ml |
| *C. albicans* ATCC 10231 | 1.0 μl/ml |

TABLE 7-continued

Minimum Inhibitory Concentration (MIC)
(sample/ml of agar or broth)

| | Antimicrobial Agent of Example 4 |
|---|---|
| *P. aeruginosa* ATCC 27853 | 5.5 μl/ml |
| *A. niger* ATCC 16404 | 1.0 μl/ml |

While various embodiments have been selected to demonstrate the invention, it will be understood that various changes and modifications can be made without departing from the scope of the invention as defined in the appended claims.

What is claimed is:

1. A process for inhibiting the growth of microorganisms, said process comprising the step of contacting said microorganisms with an effective amount of an antimicrobial agent, said antimicrobial agent including a mixture of plant materials comprising about 20 wt % to 40 wt % *Origanum vulgare* L., about 20 wt % to 40 wt % *Thymus vulgaris* L., about 10 wt % to 30 wt % *Rosmarinus officinalis* L., and about 5 wt % to 15 wt % *Lavandula officinalis* L.

2. The process of claim 1, wherein said plant materials are present in substantially equal amounts.

3. The process of claim 1, wherein said antimicrobial agent further comprises *Cinnamomum zeylanicum* Nees.

4. The process of claim 1, wherein said antimicrobial agent further comprises *Hydrastis canadensis* L.

5. The process of claim 1, wherein said microorganisms are on a substrate capable of supporting growth of microorganisms and said process comprises contacting said substrate with said antimicrobial agent.

6. The process of claim 1, wherein said microorganisms are in or on a base material capable of supporting the growth of said microorganisms and where said process comprises dispersing said antimicrobial agent in or on said base material.

7. The process of claim 6, wherein said substrate is a food product.

8. The process of claim 1, wherein said composition further comprises a food compatible carrier.

9. The process of claim 1, wherein said antimicrobial agent further comprises olive leaf extract.

10. The process of claim 1, wherein said antimicrobial agent further comprises about 5 wt % to 15 wt % *Cinnamomum zeylanicum* Nees.

11. The process of claim 1, wherein said antimicrobial agent further comprises about 0.001 wt % to 0.003 wt % *Hydrastis canadensis* L.

12. The process of claim 11, wherein said antimicrobial agent further comprises about 0.001 wt % to about 0.005 wt % olive leaf extract.

13. The process of claim 1, wherein said antimicrobial agent is combined with a component selected from the group consisting of anti-caking agents, flavoring agents, dispersing agents, emulsifying agents and mixtures thereof.

14. The process of claim 1, wherein said microorganisms are mold, bacteria or fungi.

15. The process of claim 1, wherein said antimicrobial agent comprises extracts of said plant materials in amounts effective to inhibit growth of said microorganisms.

16. The process of claim 1, wherein said plant materials are present in amounts to provide a microorganism-inhibiting amount of a compound selected from the group consisting of carvacrol, thymol, cinnamaldehyde, eugenol, cineole, camphor, α-pinene, rosmarinic acid, linalol, linalyl acetate, berberine and hydrastine, and mixtures thereof.

17. A shelf-stable composition, comprising:
a base material capable of supporting the growth of microorganisms, and
an effective amount of an antimicrobial agent to inhibit the growth of microorganisms on or in said substrate, said antimicrobial agent including a mixture of plant materials comprising about 20 wt % to 40 wt % *Origanum vulgare* L., about 20 wt % to 40 wt % *Thymus vulgaris* L., about 10 wt % to 30 wt % *Rosmarinus officinalis* L., and about 5 wt % to 15 wt % *Lavandula officinalis* L.

18. The shelf-stable composition of claim 17, wherein said antimicrobial agent further comprises an effective amount of *Cinnamomum zeylanicum* Nees to inhibit the growth of microorganisms.

19. The shelf-stable composition of claim 17, wherein said antimicrobial agent further comprises an effective amount of *Hydrastis canadensis* L. to inhibit the growth of microorganisms.

20. The shelf-stable composition of claim 17, wherein said antimicrobial agent is a coating on said base material.

21. The shelf-stable composition of claim 17, wherein said antimicrobial agent is dispersed in said base material.

22. The shelf-stable composition of claim 17, wherein said base material is a liquid, solid, or semi-solid.

23. The shelf-stable composition of claim 17, wherein said base material is a food product.

24. The shelf-stable composition of claim 17, wherein said base material is a food product and said antimicrobial agent is dispersed in a food-compatible carrier that is in contact with said food product.

25. The shelf-stable composition of claim 17, wherein said antimicrobial agent is admixed with a component selected from the group consisting of anti-caking agents, flavoring agents, dispersing agents, emulsifying agents, and mixtures thereof.

26. The shelf-stable composition of claim 17, wherein said antimicrobial agent comprises extracts of said plant material in amounts sufficient to inhibit the growth of microorganisms.

27. The shelf-stable composition of claim 17, wherein said antimicrobial agent further comprises an effective amount of olive leaf extract to inhibit the growth of microorganisms.

28. The shelf-stable composition of claim 17, wherein said plant materials are included in amounts to provide a microorganism inhibiting amount of a compound selected from the group consisting of carvacrol, thymol, cinnamaldehyde, eugenol, cineole, camphor, α-pinene, rosmarinic acid, linalol, linalyl acetate, berberine and hydrastine, and mixtures thereof.

29. The shelf-stable composition of claim 17, wherein said plant materials are selected from the group consisting of leaves, stems, flowers, extracts and mixtures thereof.

30. The shelf-stable composition of claim 17, wherein said antimicrobial agent further comprises about 5 wt % to 15 wt % *Cinnamomum zeylanicum* Nees.

31. The shelf-stable composition of claim 17, wherein said antimicrobial agent further comprises about 0.001 wt % to 0.003 wt % *Hydrastis canadensis* L.

32. The shelf-stable composition of claim 17, wherein said antimicrobial agent further comprises about 0.001 wt % to about 0.005 wt % olive leaf extract.

33. A preservative and stabilizing composition, comprising: an antimicrobial agent comprising a mixture of plant material extracts of about 20 wt % to 40 wt % *Origanum vulgare* L., about 20 wt % to 40 wt % *Thymus vulgaris* L., about 10 wt % to 30 wt % *Rosmarinus officinalis* L., and about 5 wt % to 15 wt % *Lavandula officinalis* L. in amounts effective to provide an antimicrobial effect, and
a carrier for said antimicrobial agent, wherein said antimicrobial agent is present in said carrier in an amount effective to inhibit the growth of microorganisms.

34. The composition of claim 33, wherein said antimicrobial agent is effective in inhibiting the growth of fungi, bacteria, mold or yeasts.

35. The composition of claim 33, wherein said antimicrobial agent is effective in inhibiting the growth of microorganisms selected from the group consisting of gram-positive *Staphylococcus aureus*, gram-negative *Escherichia coil, Salmonella typhimurium, Klebsiella pneumoniae*, and *Pseudomonas aeruginosa*, acid-fast bacterium *Mycobacterium smegmatis*, the yeast *Candida albicans*, and *Aspergillus niger*.

36. The composition of claim 33, wherein said carrier is a liquid, solid, gel or paste.

37. The composition of claim 33, further comprising a component selected from the group consisting of anti-caking agents, flavoring agents, dispersing agents, emulsifying agents, and mixtures thereof.

38. The composition of claim 33, wherein said plant materials are present in amounts to provide a microorganism inhibiting amount of a compound selected from the group consisting of carvacrol, thymol, cinnamaldehyde, eugenol, cineole, camphor, α-pinene, rosmarinic acid, linalol, linalyl acetate, berberine and hydrastine, and mixtures thereof.

39. The composition of claim 33, wherein said antimicrobial agent further comprises an effective amount of *Hydrastis canadensis* L.

40. The composition of claim 33, wherein said antimicrobial agent further comprises about 0.001 wt % to about 0.005 wt % olive leaf extract.

41. The composition of claim 33, wherein said antimicrobial agent further comprises about 5 wt % to 15 wt % *Cinnamomum zeylanicum* Nees.

42. The composition of claim 33, wherein said antimicrobial agent further comprises about 0.001 wt % to 0.003 wt % *Hydrastis canadensis* L.

* * * * *